US009226782B2

(12) United States Patent
Simonson et al.

(10) Patent No.: US 9,226,782 B2
(45) Date of Patent: *Jan. 5, 2016

(54) INSTRUMENTS AND METHODS FOR MINIMALLY INVASIVE SPINE SURGERY

(71) Applicant: DePuy Synthes Products, Inc., Raynham, MA (US)

(72) Inventors: Robert E Simonson, Boca Raton, FL (US); Timothy Allen Beardsley, Kingston, MA (US); Douglas Scott Bireley, Basel-Landschaft (CH)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/889,768

(22) Filed: May 8, 2013

(65) Prior Publication Data

US 2013/0245382 A1 Sep. 19, 2013

Related U.S. Application Data

(63) Continuation of application No. 12/909,158, filed on Oct. 21, 2010, now Pat. No. 8,444,678, which is a continuation of application No. 10/914,983, filed on Aug. 10, 2004, now Pat. No. 7,824,410, which is a
(Continued)

(51) Int. Cl.
*A61B 17/88* (2006.01)
*A61B 1/32* (2006.01)
(Continued)

(52) U.S. Cl.
CPC ........... *A61B 17/7083* (2013.01); *A61B 17/025* (2013.01); *A61M 29/00* (2013.01);
(Continued)

(58) Field of Classification Search
CPC ............. A61B 17/025; A61B 17/7083; A61B 17/0218; A61B 17/3417; A61B 17/3421; A61B 2017/3443; A61B 2017/0256; A61B 2019/462; A61M 29/00; A61M 29/02
USPC ........................ 600/210, 204, 235, 203, 201; 606/246–256, 96, 190, 99, 90, 191, 606/279, 86 A, 914
See application file for complete search history.

(56) References Cited

U.S. PATENT DOCUMENTS

| 569,839 A | 10/1896 | Roeloffs |
| 1,633,703 A | 6/1927 | Kaji |

(Continued)

FOREIGN PATENT DOCUMENTS

| WO | WO 0018306 | 4/2000 |
| WO | WO 02060330 | 8/2002 |

OTHER PUBLICATIONS

Barone, "An Improved Retractor for the Anterior Apporach in the Surgical Management of Vertebral Fractures," Am J Orthop, 1998, pp. 703-704, vol. 27(10).
(Continued)

*Primary Examiner* — Pedro Philogene (57) ABSTRACT

A system for minimally invasive spine surgery includes a plurality of bone anchors, a spinal rod, a plurality of dilators of differing lengths and diameters, and a surgical access port. The surgical access port includes a proximal end, a distal end, and a sidewall defining a lumen extending from the proximal end to the distal end. The port may include a first opening formed in the sidewall that defines a passageway for medical hardware from the lumen to external to the port. The system can include first instrument for creating a subcutaneous pathway from the opening in the port.

9 Claims, 7 Drawing Sheets

Related U.S. Application Data continuation-in-part of application No. 10/021,809, filed on Oct. 30, 2001, now Pat. No. 7,008,431, and a continuation-in-part of application No. 10/024,221, filed on Oct. 30, 2001, now Pat. No. 6,916,330.

(51) Int. Cl.

| | |
|---|---|
| *A61B 17/70* | (2006.01) |
| *A61M 29/00* | (2006.01) |
| *A61M 29/02* | (2006.01) |
| *A61B 17/02* | (2006.01) |
| *A61B 17/34* | (2006.01) |
| *A61B 19/00* | (2006.01) |

(52) U.S. Cl.
CPC ........... *A61M 29/02* (2013.01); *A61B 17/0218* (2013.01); *A61B 17/3417* (2013.01); *A61B 17/3421* (2013.01); *A61B 2017/0256* (2013.01); *A61B 2017/3443* (2013.01); *A61B 2019/462* (2013.01)

(56) References Cited

U.S. PATENT DOCUMENTS

| | | |
|---|---|---|
| 2,922,420 A | 1/1960 | Cheng |
| 3,470,872 A | 10/1969 | Grieshaber |
| 3,875,595 A | 4/1975 | Froning |
| 4,232,660 A | 11/1980 | Coles |
| 4,440,168 A | 4/1984 | Warren |
| 4,449,532 A | 5/1984 | Storz |
| 4,481,947 A | 11/1984 | Chester |
| 4,545,374 A | 10/1985 | Jacobson |
| 4,573,448 A | 3/1986 | Kambin |
| 4,617,922 A | 10/1986 | Griggs |
| 4,620,460 A | 11/1986 | Gonzales, Jr. |
| 4,686,972 A | 8/1987 | Kurland |
| 4,736,738 A | 4/1988 | Lipovsek |
| 4,747,394 A | 5/1988 | Watanabe |
| 4,798,111 A | 1/1989 | Cheeseman |
| 4,803,976 A | 2/1989 | Frigg |
| 4,808,157 A | 2/1989 | Coombs |
| 4,817,587 A | 4/1989 | Janese |
| 4,862,891 A | 9/1989 | Smith |
| 4,863,423 A | 9/1989 | Wallace |
| 4,872,451 A | 10/1989 | Moore |
| 4,882,958 A | 11/1989 | McNeeley |
| 4,952,214 A | 8/1990 | Comparetto |
| 4,969,888 A | 11/1990 | Scholten |
| 5,035,232 A | 7/1991 | Lutze |
| 5,048,379 A | 9/1991 | Gramera |
| 5,052,373 A | 10/1991 | Michelson |
| 5,084,043 A | 1/1992 | Hertzmann |
| 5,098,435 A | 3/1992 | Stednitz |
| 5,106,376 A | 4/1992 | Mononen |
| 5,133,720 A | 7/1992 | Greenberg |
| 5,135,525 A | 8/1992 | Biscoping |
| 5,148,724 A | 9/1992 | Rexford |
| 5,158,543 A | 10/1992 | Lazarus |
| 5,171,279 A | 12/1992 | Mathews |
| 5,195,541 A | 3/1993 | Obenchain |
| 5,242,443 A | 9/1993 | Kambin |
| 5,275,611 A | 1/1994 | Behl |
| 5,279,567 A | 1/1994 | Ciaglia |
| 5,292,309 A | 3/1994 | Van Tassel |
| 5,303,694 A | 4/1994 | Mikhail |
| 5,312,360 A | 5/1994 | Behl |
| 5,342,384 A | 8/1994 | Sugarbaker |
| 5,356,413 A | 10/1994 | Martins |
| 5,363,841 A | 11/1994 | Coker |
| 5,403,264 A | 4/1995 | Wohlers |
| 5,431,639 A | 7/1995 | Shaw |
| 5,431,651 A | 7/1995 | Goble |
| D361,381 S | 8/1995 | Koros |
| 5,439,464 A | 8/1995 | Shapiro |
| 5,472,426 A | 12/1995 | Bonati |
| 5,489,274 A | 2/1996 | Chu |
| 5,512,038 A | 4/1996 | O'Neal |
| 5,562,677 A | 10/1996 | Hildwein |
| 5,569,248 A | 10/1996 | Mathews |
| 5,601,550 A | 2/1997 | Esser |
| 5,611,778 A | 3/1997 | Brinon |
| 5,687,739 A | 11/1997 | McPherson |
| 5,716,415 A | 2/1998 | Steffee |
| 5,728,097 A | 3/1998 | Mathews |
| 5,743,853 A | 4/1998 | Lauderdale |
| 5,746,720 A | 5/1998 | Stouder, Jr. |
| 5,766,221 A | 6/1998 | Benderev |
| 5,792,044 A | 8/1998 | Foley |
| D399,955 S | 10/1998 | Koros |
| 5,816,257 A | 10/1998 | Chin |
| RE36,020 E | 12/1998 | Moore |
| 5,851,207 A | 12/1998 | Cesarone |
| 5,882,344 A | 3/1999 | Stouder, Jr. |
| 5,885,299 A | 3/1999 | Winslow |
| 5,885,300 A | 3/1999 | Tokuhashi |
| 5,891,147 A | 4/1999 | Moskovitz |
| 5,895,352 A | 4/1999 | Kleiner |
| 5,895,390 A | 4/1999 | Moran |
| 5,897,593 A | 4/1999 | Kohrs |
| 5,899,901 A | 5/1999 | Middleton |
| 5,902,231 A | 5/1999 | Foley |
| 5,913,818 A | 6/1999 | Co |
| 5,928,139 A | 7/1999 | Koros |
| 5,944,658 A | 8/1999 | Koros |
| 5,954,635 A | 9/1999 | Foley |
| 5,954,671 A | 9/1999 | O'Neill |
| 5,967,970 A | 10/1999 | Cowan |
| 5,971,920 A | 10/1999 | Nagel |
| 5,976,146 A | 11/1999 | Ogawa |
| 5,996,447 A | 12/1999 | Bayouth |
| 6,004,322 A | 12/1999 | Bernstein |
| 6,007,487 A | 12/1999 | Foley |
| 6,010,520 A | 1/2000 | Pattison |
| 6,033,406 A | 3/2000 | Mathews |
| 6,063,088 A | 5/2000 | Winslow |
| 6,080,155 A | 6/2000 | Michelson |
| 6,081,741 A | 6/2000 | Hollis |
| 6,083,225 A | 7/2000 | Winslow |
| 6,113,602 A | 9/2000 | Sand |
| 6,120,434 A | 9/2000 | Kimura |
| 6,120,506 A | 9/2000 | Kohrs |
| D433,296 S | 11/2000 | Yamakawa |
| 6,152,871 A | 11/2000 | Foley |
| 6,156,006 A | 12/2000 | Brosens |
| 6,159,179 A | 12/2000 | Simonson |
| 6,162,170 A | 12/2000 | Foley |
| 6,162,236 A | 12/2000 | Osada |
| D436,513 S | 1/2001 | Yamakawa |
| 6,176,823 B1 | 1/2001 | Foley |
| D438,074 S | 2/2001 | Marr |
| 6,197,002 B1 | 3/2001 | Peterson |
| 6,206,822 B1 | 3/2001 | Foley |
| 6,206,826 B1 | 3/2001 | Mathews |
| 6,206,885 B1 | 3/2001 | Ghahremani |
| 6,214,004 B1 | 4/2001 | Coker |
| 6,217,509 B1 | 4/2001 | Foley |
| 6,224,597 B1 | 5/2001 | Coker |
| 6,224,608 B1 | 5/2001 | Ciccolella |
| 6,241,734 B1 | 6/2001 | Scribner |
| 6,245,072 B1 | 6/2001 | Zdeblick |
| 6,258,097 B1 | 7/2001 | Cook |
| 6,267,763 B1 | 7/2001 | Castro |
| 6,270,498 B1 | 8/2001 | Michelson |
| 6,273,896 B1 | 8/2001 | Franck |
| 6,283,966 B1 | 9/2001 | Houfburg |
| 6,287,313 B1 | 9/2001 | Sasso |
| 6,296,609 B1 | 10/2001 | Brau |
| 6,312,432 B1 | 11/2001 | Leppelmeier |

(56) References Cited

U.S. PATENT DOCUMENTS

| | | |
|---|---|---|
| 6,342,057 B1 | 1/2002 | Brace |
| 6,348,058 B1 | 2/2002 | Melkent |
| 6,354,176 B1 | 3/2002 | Nordlin |
| 6,371,959 B1 | 4/2002 | Trice |
| 6,371,968 B1 | 4/2002 | Kogasaka |
| 6,395,007 B1 | 5/2002 | Bhatnagar |
| 6,418,821 B1 | 7/2002 | Yamakawa |
| 6,428,472 B1 | 8/2002 | Haas |
| 6,461,330 B1 | 10/2002 | Miyagi |
| D466,766 S | 12/2002 | Marty |
| 6,520,907 B1 * | 2/2003 | Foley et al. ............... 600/114 |
| 6,524,238 B2 | 2/2003 | Velikaris |
| 6,530,926 B1 | 3/2003 | Davison |
| 6,530,929 B1 | 3/2003 | Justis |
| 6,540,756 B1 | 4/2003 | Vaughan |
| 6,558,386 B1 | 5/2003 | Cragg |
| 6,607,530 B1 | 8/2003 | Carl |
| 6,692,434 B2 | 2/2004 | Ritland |
| 6,793,656 B1 | 9/2004 | Mathews |
| 6,916,330 B2 | 7/2005 | Simonson |
| 6,921,403 B2 | 7/2005 | Cragg |
| 6,929,606 B2 | 8/2005 | Ritland |
| 7,008,424 B2 | 3/2006 | Teitelbaum |
| 7,008,431 B2 | 3/2006 | Simonson |
| 7,435,219 B2 | 10/2008 | Kim |
| 7,476,240 B2 * | 1/2009 | Raymond et al. ............ 606/279 |
| 7,491,218 B2 * | 2/2009 | Landry et al. .............. 606/246 |
| 7,527,638 B2 * | 5/2009 | Anderson et al. ............ 606/279 |
| 7,547,318 B2 * | 6/2009 | Birkmeyer et al. ........... 606/279 |
| 7,588,588 B2 * | 9/2009 | Spitler et al. ............... 606/246 |
| 7,648,506 B2 | 1/2010 | McCord |
| 7,648,507 B2 | 1/2010 | Techiera |
| 7,666,188 B2 * | 2/2010 | Anderson et al. ............ 606/104 |
| 7,824,410 B2 | 11/2010 | Simonson |
| RE42,525 E | 7/2011 | Simonson |
| 8,192,437 B2 | 6/2012 | Simonson |
| 8,235,999 B2 | 8/2012 | Simonson |
| 8,361,151 B2 | 1/2013 | Simonson |
| 8,444,678 B2 * | 5/2013 | Simonson et al. ........... 606/279 |
| 8,556,905 B2 | 10/2013 | Simonson |
| 8,852,244 B2 | 10/2014 | Simonson |
| 2001/0012942 A1 | 8/2001 | Estes |
| 2001/0027320 A1 | 10/2001 | Sasso |
| 2002/0011135 A1 | 1/2002 | Hall |
| 2002/0016592 A1 | 2/2002 | Branch |
| 2002/0022764 A1 | 2/2002 | Smith |
| 2002/0045904 A1 | 4/2002 | Fuss |
| 2002/0049368 A1 | 4/2002 | Ritland |
| 2002/0058948 A1 | 5/2002 | Arlettaz |
| 2002/0077632 A1 | 6/2002 | Tsou |
| 2002/0082695 A1 | 6/2002 | Neumann |
| 2002/0088695 A1 | 7/2002 | Migimatsu |
| 2002/0123668 A1 | 9/2002 | Ritland |
| 2002/0143235 A1 | 10/2002 | Pagliuca |
| 2002/0161368 A1 | 10/2002 | Foley |
| 2003/0083688 A1 | 5/2003 | Simonson |
| 2003/0083689 A1 | 5/2003 | Simonson |
| 2003/0187431 A1 | 10/2003 | Simonson |
| 2003/0220689 A1 | 11/2003 | Ritland |
| 2003/0236447 A1 | 12/2003 | Ritland |
| 2004/0106997 A1 | 6/2004 | Lieberson |
| 2005/0004593 A1 | 1/2005 | Simonson |
| 2005/0080418 A1 | 4/2005 | Simonson |
| 2005/0085813 A1 | 4/2005 | Spitler |
| 2005/0131421 A1 | 6/2005 | Anderson |
| 2005/0136085 A1 | 6/2005 | Bellamy |
| 2005/0137461 A1 | 6/2005 | Marchek |
| 2005/0203490 A1 | 9/2005 | Simonson |
| 2005/0216002 A1 | 9/2005 | Simonson |
| 2007/0134175 A1 | 6/2007 | Bellamy |
| 2010/0222824 A1 | 9/2010 | Simonson |
| 2011/0040333 A1 | 2/2011 | Simonson |
| 2013/0184533 A1 | 7/2013 | Simonson |
| 2013/0245382 A1 | 9/2013 | Simonson |
| 2014/0051931 A1 | 2/2014 | Simonson |
| 2014/0371538 A1 | 12/2014 | Simonson |

OTHER PUBLICATIONS

Frank, "Endoscopic Dural Retractor for Spinal Stenosis Surgery," Minim Invasive Neurosurg, 2002, pp. 136-138, vol. 45(3).
Hilton, Donald et al, "Medtronic Sofamor Danek METRX Microdiscectomy Surgical Technique Brochure", 2001.
Hsu, Ken et al, "Internal Fixation with Pedicle Screws," Lumbar Spine Surgery, Techniques and Complications, The C. V. Mosby Company pp. 322-338 (1987).
Kambin, Parvis and Schaffer, Johnathan, "Arthroscopic Fusion of the Lumbosacral Spine," Lumbosacral and Spinopelvic Fixation, ch 44, pp. 565-577 (1996).
Kambin, Parvis, "Arthroscopic Lumbar Intervertebral Fusion," The Adult Spine: Principles and Practice, ch. 95, pp. 2037-2046 (1997).
Kambin, Parvis, "Arthroscopic Techniques for Spinal Surgery," Operative Arthroscopy, ch 89, pp. 1215-1225 (1996).
Kambin, Parviz, "Arthroscopic Microdiscectomy: Minimal Intervention in Spinal Surgery", National Library of Medicine, 1991, p. 67-100, Urban & Schwarzenberg.
Kambin, Parviz, "Percutaneous Posterolateral Discectomy", Clinical Orthopaedics and Related Research, Section II, pp. 145-154 (1986).
Kambin, Parviz, "Posterolateral Percutaneous Lumbar Interbody Fusion", Arthroscopic Microdiscectomy: Minimal Intervention in Spinal Surgery, pp. 117-121 (1991).
Leu, Hansjoerg Franz et al, "Lumber Percutaneous Endoscopic Interbody Fusion," Clinical Orthopaedics and Related Research, No. 337, pp. 58-63 (1997).
Leu, Hans-Jorg and Schreiber, Adam, "La Nucleotomie Percutanee Avec Discoscopie: Experiences Depuis 1979 Et Possibilities Actuelles," Revue Medicale De La Suisse Romande, vol. 109, pp. 477-482 (1989).
Leu, Hans-Jorg and Schreiber, Adam, "Percutaneous Lumbar Restabilization," Arthroscopic Microdiscectomy: Minimal Intervention in Spinal Surgery, pp. 123-125 (1990).
Ozer, "A New Retractor for the Anterior Cervical Approach," Br J Neurosurg, 1994, pp. 469-470, vol. 8(4).
Savitz, Martin, "Same-Day Microsurgical Arthroscopic Latera-Approach Laser-Assisted (SMALL) Fluoroscopic Discectomy", Journal of Neurosurgery, Jun. 1994, pp. 1039-1045.
Schaffer, Johnathan et al, "Percutaneous Posterolateral Lumbar Discectomy and decompression with a 6.9 Millimeter Cannula", The Journal of Bone and Joint Surgery, 1991, pp. 822-831.
Schetrumpf, Jr., "Combined Retractor and Sucker with Built-in Clearing Device for Spinal Surgery," Injury, 1973, pp. 352-353, vol. 4(4).
Schreiber, et al., "Does Percutaneous Nucleotomy with Discoscopy Replace Conventional Discectomy?", Clinical Orthopaedics and Related Research, No. 238, Jan. 1989.
Sofamor Danek Video Systems Brochure, 10 pages (1994).
Sofamor Danek, "MED MicroEndoscopic Discectomy System" (1997).
Styf, "The Effects of External Compression by Three Different Retractors on Pressure in the Erector Spine Muscles During and After Posterior Lumbar Spine Surgery in Humans," Spine, 1998, pp. 354-358, vol. 23(3), Lippincott-Raven Publishers.
Web page, http://brainlab.com, Apr. 2, 2002.
Wiltse, "New Uses and Refinements of the Paraspinal Approach to the Lumbar Spine", Spine, vol. 13 No. 6 1988, pp. 696-706.
Wolfhard Caspar, Technique of Microsurgery, in Microsugery of the Lumbar Spine: Principles and Techniques in Spine Surgery 105-122 (Aspen Publications, 1990).
Advisory Action in U.S. Appl. No. 10/899,707 dated Mar. 29, 2006.
Amendment in U.S. Appl. No. 10/899,707 dated Feb. 5, 2005.
Amendment in U.S. Appl. No. 10/899,707 dated Jul. 5, 2005.
Amendment in U.S. Appl. No. 10/899,707 dated Mar. 13, 2006.
Amendment in U.S. Appl. No. 10/899,707 dated Nov. 16, 2005.
Amendment in U.S. Appl. No. 10/899,707 dated Feb. 1, 2011.
Amendment in U.S. Appl. No. 10/899,707 dated May 19, 2011.
Appeal Brief in U.S. Appl. No. 10/899,707 dated May 31, 2006.
Amendment in U.S. Appl. No. 10/899,707 dated Dec. 2, 2011.

(56) References Cited

OTHER PUBLICATIONS

Board of Patent Appeals and Interferences Decision in U.S. Appl. No. 10/899,707 dated Dec. 2, 2010.
Patent Trial and Appeal Board Decision in U.S. Appl. No. 10/899,707 dated Dec. 4, 2012.
Examiner's Answer in U.S. Appl. No. 10/899,707 dated Dec. 13, 2006.
Examiner's Answer in U.S. Appl. No. 10/899,707 dated May 10, 2012.
Office Action in U.S. Appl. No. 10/899,707 dated Aug. 16, 2005.
Office Action in U.S. Appl. No. 10/899,707 dated Dec. 8, 2004.
Office Action in U.S. Appl. No. 10/899,707 dated Feb. 7, 2006.
Office Action in U.S. Appl. No. 10/899,707 dated Mar. 31, 2005.
Office Action in U.S. Appl. No. 10/899,707 dated Mar. 15, 2011.
Office Action in U.S. Appl. No. 10/899,707 dated Jun. 20, 2011.
Office Action in U.S. Appl. No. 12/971,929 dated Nov. 23, 2011.
Office Action in U.S. Appl. No. 10/899,707 dated Dec. 14, 2011.
Office Action in U.S. Appl. No. 12/971,929 dated Apr. 26, 2012.
Office Action in U.S. Appl. No. 10/899,707 dated Mar. 14, 2013. (11 pages).
Reply Brief in U.S. Appl. No. 10/899,707 dated Feb. 7, 2007.
Amendment filed in U.S. Appl. No. 12/971,929 on Aug. 7, 2013.
Amendment filed in U.S. Appl. No. 12/971,929 on Feb. 23, 2012.
Amendment filed in U.S. Appl. No. 12/971,929 on Jun. 29, 2012.
Office Action in U.S. Appl. No. 12/971,929 dated Feb. 8, 2013.
Office Action in U.S. Appl. No. 12/971,929 dated Oct. 10, 2013.
Office Action in U.S. Appl. No. 14/026,536 dated Jan. 15, 2014.
Office Action in U.S. Appl. No. 10/899,707 dated Mar. 20, 2014.
Office Action in U.S. Appl. No. 10/899,707 dated Oct. 7, 2013.
Office Action in U.S. Appl. No. 12/971,929 dated May 7, 2014.
Amendment filed in U.S. Appl. No. 12/971,929 on Mar. 27, 2014.
Amendment filed in U.S. Appl. No. 14/026,536 on May 15, 2014.
Final Office Action in U.S. Appl. No. 12/971,929 dated Oct. 27, 2014.
Amendment filed in U.S. Appl. No. 12/971,929 on Aug. 5, 2014.
Amendment filed in U.S. Appl. No. 12/971,929 on Jan. 20, 2015.

* cited by examiner

INSTRUMENTS AND METHODS FOR MINIMALLY INVASIVE SPINE SURGERY

CROSS REFERENCE TO RELATED APPLICATIONS

This application is a continuation of U.S. patent application Ser. No. 12/909,158, filed Oct. 21, 2010, which is a continuation of Ser. No. 10/914,983, filed Aug. 10, 2004, which is a continuation-in-part of U.S. patent application Ser. No. 10/021,809, filed Oct. 30, 2001, and is a continuation-in-part of U.S. patent application Ser. No. 10/024,221, filed Oct. 30, 2001. Each of the aforementioned patent applications is incorporated herein by reference.

BACKGROUND

For a number of known reasons, spinal fixation devices are used in orthopedic surgery to align and/or fix a desired relationship between adjacent vertebral bodies. Such devices typically include a spinal fixation element, such as a relatively rigid fixation rod or plate, that is coupled to adjacent vertebrae by attaching the element to various anchoring devices, such as hooks, bolts, wires, or screws. The fixation elements can have a predetermined contour that has been designed according to the properties of the target implantation site, and once installed, the fixation element holds the vertebrae in a desired spatial relationship, either until desired healing or spinal fusion has taken place, or for some longer period of time.

Spinal fixation elements can be anchored to specific portions of the vertebrae. A variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, often in the form of a U-shaped recess formed in the head. A set-screw, plug, or similar type of closure mechanism is used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other closure mechanism to securely interconnect each screw and the fixation rod.

Recently, the trend in spinal surgery has been moving toward providing minimally invasive devices and methods for implanting bone anchors and spinal fixation devices. One such method, for example, is disclosed in U.S. Pat. No. 6,530,929 of Justis et al. and it utilizes two percutaneous access devices for implanting an anchoring device, such as a spinal screw, into adjacent vertebrae. A spinal rod is then introduced through a third incision a distance apart from the percutaneous access sites, and the rod is transversely moved into the rod-engaging portion of each spinal screw. The percutaneous access devices can then be used to apply closure mechanisms to the rod-engaging heads to lock the rod therein. While this procedure offers advantages over prior art invasive techniques, the transverse introduction of the rod can cause significant damage to surrounding tissue and muscle.

Accordingly, there remains a need for improved minimally invasive devices and methods for treatment of spinal disorders.

SUMMARY

Disclosed herein are instruments and methods that facilitate the treatment of spinal disorders in a minimally invasive manner. In particular, the disclosed methods permit the delivery and implanting of one or more bone anchors and/or one or more fixation elements, for example, a spinal rod, in a minimally invasive manner thereby limiting trauma to surrounding tissue. Moreover, certain exemplary methods disclosed herein facilitate the removal of diseased disc material and the placement of an interbody fusion device to promote spinal fusion, on one or both sides of the spine, in a minimally invasive manner. Also, disclosed herein are instruments that facilitate the subcutaneous delivery and connection of a fixation element, such as a spinal rod, to a bone anchor.

In one exemplary embodiment, an exemplary minimally invasive surgical method comprises making a first incision in a patient, positioning a first port in the first incision, advancing a distal end of the port into proximity to a vertebra, and positioning an instrument through an opening proximate the distal end of the port.

In one exemplary embodiment, an exemplary minimally invasive surgical method comprises inserting a first port that defines a first pathway to a first vertebra, advancing a first anchor through the first port to the first vertebra, inserting a second port that defines a second pathway to a second vertebra, advancing a second anchor through the second port to the second vertebra, positioning a first end of a fixation element in the first port, and advancing the first end of the fixation element subcutaneously through an opening in the first port and an opening in second port to the second anchor.

In one exemplary embodiment, an exemplary minimally invasive surgical method comprises making a first incision in a patient, positioning a first port in the first incision, advancing a first anchor through a first pathway defined by the first port to a first anchor site on the first vertebra, making a second incision in the patient, positioning a second port in the second incision, advancing a second anchor through a second pathway defined by the second port to a second anchor site on the second vertebra, positioning a first end of a fixation element in the first port, advancing the first end of the fixation element subcutaneously through an opening in the first port and an opening in second port to the second anchor, and coupling the fixation element to the first anchor and the second anchor.

In one exemplary embodiment, an exemplary surgical access port comprises a proximal end, a distal end spaced apart a distance from the proximal end and a sidewall defining a lumen extending from the proximal end to the distal end. In the exemplary port, the lumen has a length sufficient to at least span from a skin incision to proximate a vertebra. The exemplary port may include a first opening formed in the sidewall that defines a passageway for medical hardware from the lumen to external to the port.

In one exemplary embodiment, a system for minimally invasive spine surgery comprises a first dilator having a first diameter and a surgical access port. In the exemplary system, the port may comprise a proximal end, a distal end spaced apart a distance from the proximal end, and a sidewall defining a lumen extending from the proximal end to the distal end. In the exemplary system, the lumen of the port may have a length sufficient to at least span from a skin incision to proximate a vertebra and may have a diameter greater than the first diameter. The exemplary port may have a first opening formed in the sidewall that defines a passageway for medical hardware from the lumen to external to the port.

BRIEF DESCRIPTION OF THE DRAWINGS

These and other features and advantages of the methods and instruments disclosed herein will be more fully understood by reference to the following detailed description in conjunction with the attached drawings in which like reference numerals refer to like elements through the different views. The drawings illustrate principles of the methods and instruments disclosed herein and, although not to scale, show relative dimensions.

DETAILED DESCRIPTION

Certain exemplary embodiments will now be described to provide an overall understanding of the principles of the structure, function, manufacture, and use of the instruments and methods disclosed herein. One or more examples of these embodiments are illustrated in the accompanying drawings. Those of ordinary skill in the art will understand that the instruments and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

Figure 1:
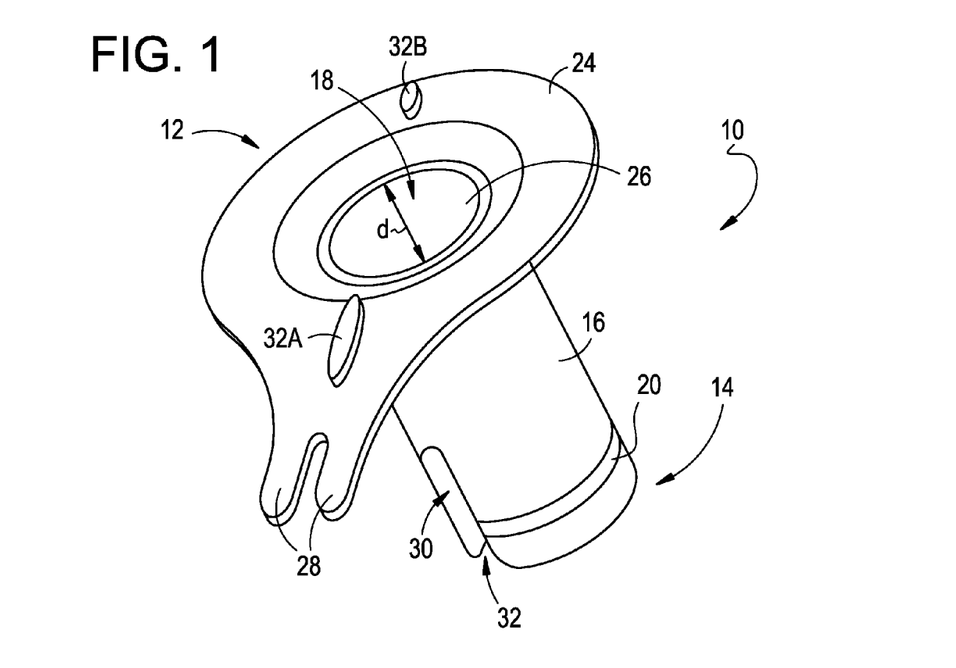
FIG. 1 is a perspective view of an exemplary embodiment of a surgical access port, illustrating an opening formed in a sidewall of the port.
Figure 2:
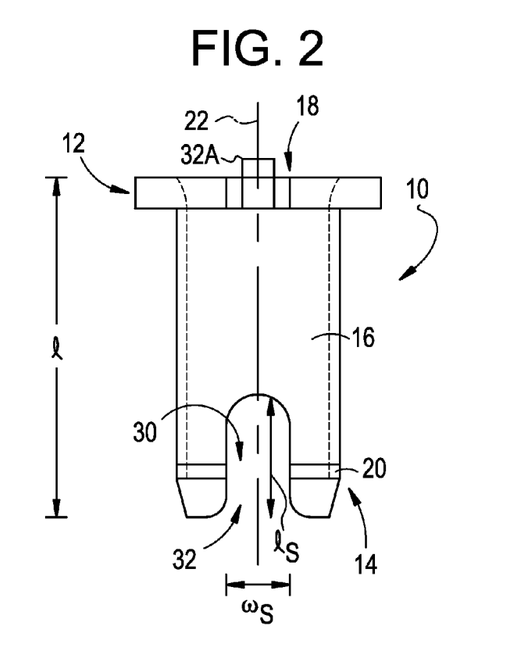
FIG. 2 is a side view of the surgical access port of FIG. 1.
Figure 3:
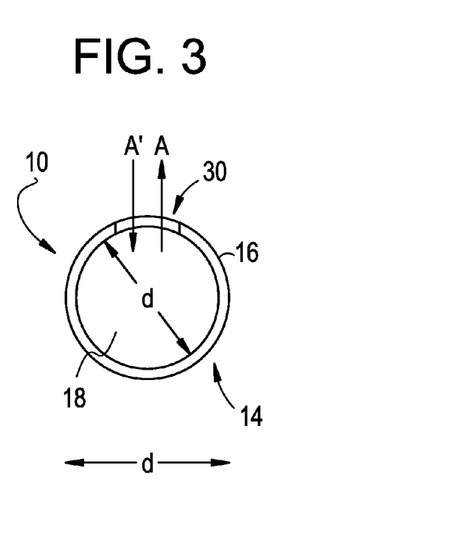
FIG. 3 is a bottom view of the surgical access port of FIG. 1.

FIGS. 1-3 illustrate an exemplary embodiment of a surgical access port 10 for providing posterior, lateral, or anterior access to the spine. The exemplary port includes a proximal end 12, a distal end 14 spaced apart a distance from the proximal end 12 and a sidewall 16 defining a lumen 18 extending from the proximal end 12 to the distal end 14. In the exemplary embodiment, the lumen 18 has a length sufficient to at least span from a skin incision to proximate a vertebra. The exemplary port 10, in the illustrated embodiment, may include a first opening 30 formed in the sidewall 16 that defines a passageway for medical hardware, such as, for example, surgical instruments and/or implants, from the lumen to external to the port, as discussed in more detail below. The lumen 18 of the exemplary port 10 provides unobstructed access from the proximal end of the lumen 18 to the distal end of the lumen 18 to permit the advancement of instruments and/or implants through the lumen 18.

The size and shape of the exemplary port 10 may vary depending on the intended use of the port 10, for example, the region of the spine, e.g., cervical, thoracic, or lumbar, the approach, e.g., posterior, lateral, or anterior, and the type(s) of implants and instruments desired to be positioned through the lumen 18 of the port 10. In illustrated exemplary embodiments, for example, the port 10 may have a length l sufficient to span from a posterior skin incision to proximate a vertebra. The length l of the port 10 may be varied, for example, depending on whether the port 10 is designed for use in the cervical, thoracic, or lumbar spine. For example, the port 10 may have a length l that allows the proximal end 12 of the port 10 to be positioned outside the patient's body, e.g., proximal to or parallel to the level of the skin, while the distal end 14 of the port 10 is in proximity to or abuts against a posterior surface of a vertebra.

Continuing to refer to FIGS. 1-3, the exemplary port 10 may have a cross-sectional shape and size that varies depending on the intended use of the port 10, for example, the region of the spine, e.g., cervical, thoracic, or lumbar, and the type(s) of implants and instruments desired to be positioned through the lumen 18 of the port 10. In the exemplary embodiment illustrated in FIGS. 1-3, for example, the exemplary port 10 has a circular cross section. In other exemplary embodiments, such as the exemplary port 110 illustrated in FIGS. 4-6, the port 110 may have an elliptical or oval cross-section. One skilled in the art will appreciate that the port 10 may have a cross section that is circular, rectangular, square, elliptical, polygonal or any other shape suitable for providing surgical access to the spine. In the exemplary embodiments illustrated in FIGS. 1-3 and 4-6, the port 10 and the port 100 each have a generally constant cross section, e.g., the size and/or shape of the cross section of the port does not vary along the length l of the cannula. In certain other exemplary embodiments, the cross section of the port may vary in size and shape along the length l of the cannula. For example, the width or diameter of the port may vary along the length of the cannula. In the exemplary embodiments illustrated in FIGS. 1-3 and 4-6 the port 10 and the port 100 each have a continuous cross section in the manner of, for example, a cannula. In certain other embodiments, the port may have a non-continuous cross-section. For example, the port may have a C-shaped cross section or may include one or more longitudinally oriented slots that interrupt the cross section along the length l of the port. In certain exemplary embodiments, the distal end 14 of the port 10 may be sized and shaped to facilitate engagement with the anatomy of the vertebra. For example, the distal end 14 may have a beveled, tapered, and/or angled shape.

In the exemplary embodiment illustrated in FIGS. 1-3, the lumen 18 of the exemplary port 10 may have a diameter d that is sufficient to allow a spinal implant and/or instrument to be introduced therethrough. Examples of spinal implants that may be introduced through the port 10 include spinal fixation elements, such as a plate, rod, or tether, interbody fusion devices, nucleus replacement devices, artificial discs, and fasteners, such as bone anchors. The diameter d of the lumen 18 may be sized to allow any of these implants and associated instruments to be introduced therethrough. In certain exemplary embodiments, the diameter d of the exemplary port 10 may be sized to provide access to a portion of a first vertebra, for example, the pedicle, e.g., for placement of a bone anchor. In certain exemplary embodiments, the diameter d of the exemplary port 10 may be sized to span between a first vertebra and a second vertebra to provide access to the first vertebra, the second vertebra and the disk therebetween.

The exemplary port 10 may be constructed from any material suitable for use in vivo, including metals, such as stainless steel or titanium, polymers, ceramics, or composite materials.

In certain exemplary embodiments, the port 10 may be constructed from a translucent polymer. The outer surface of the sidewall 16 of the exemplary port 10 may be contoured to minimize sharp edges and, thereby, inhibit injury to muscles and tissues surrounding the port 10. In addition, the outer surface of the sidewall 16 of the port 10 may include surface texturing to facilitate holding retracted tissue in place, in particular, away from the distal end of the lumen 18. The surface texturing may be, for example, one or more annular grooves 20 formed in the outer surface of the sidewall 16 of the port 10. In certain embodiments, the surface texturing may be surface roughening, ridges, spiral grooves, and/or materials with a high coefficient of friction. In certain exemplary embodiments, the outer surface of the sidewall 16 of the port 10 is coated with silicon to facilitate holding refracted tissue.

The proximal end 12 of the exemplary port 10 may optionally include a positioning ring 24 that facilitates the positioning of the port 10. The positioning ring 24 may be generally annular in shape and may have an outer diameter that is greater that the diameter of the port 10. The positioning ring 24, in the exemplary port 10, may have a tapered opening 26 that tapers to the diameter of the lumen 16 of the port to facilitate positioning of implants and instruments into the port 10. The positioning ring 24 may include one or more tabs 28 that facilitate connection of the positioning ring 24 and, thus, the port 10, to a clamp, such as a C-arm.

The exemplary port 10 may be configured to hold a light source that illuminates the lumen 18 and/or the distal end 32 of the port 10, for example, during a procedure performed in the port 10. In one exemplary embodiment, the proximal end 12 may include a coupling mechanism, for example, a clamp, for hold one or more light sources, for example, a fiber optic cable or a light tube, that is oriented to illuminate the lumen and the distal end of the port 10. In other exemplary embodiments, one ore more light sources, for example, a fiber optic cable or a light tube, may be embedded within the sidewalls 16 of the port 10 to illuminate the lumen 18 and/or the distal end 14 of the port 10.

Continuing to refer to FIGS. 1-3, the exemplary port 10 may include one or more openings 30 formed in the sidewall 16 of the port 10. In the illustrated embodiment, for example, the port 10 includes a single opening 30 formed in the sidewall 16 of the port 10. The opening 30 defines a passageway for medical hardware, for example spinal instruments and implants, between the lumen 18 and the exterior of the port 10. For example, once the port 10 is positioned in proximity to a surgical site, medical hardware may be advanced subcutaneously from the lumen 18 to external to the port 10, as indicated by arrow A in FIG. 3. Alternatively, medical hardware may be advanced subcutaneously from exterior to the port 10 into the lumen 18 through the passageway, as indicated by arrow A' in FIG. 3.

The size, shape, position, and number of the opening(s) 30 may be varied depending on, for example, the procedure selected and the medical hardware employed. The exemplary ports 10, 110, and 210, illustrated in FIGS. 1-3, 4-6, and 12, respectively, provide examples of ports having various sized, shaped, and positioned opening(s). For example, in the exemplary embodiment illustrated in FIGS. 1-3, the opening 30 may be sized, shaped, and positioned to facilitate delivery of a spinal fixation element, such as a plate, rod, cable, or tether, to a site exterior to the port 10. The opening 30, in the exemplary port 10, is an elongated slot extending proximally from the distal end 14 of the port 10. The opening 30 is oriented generally parallel to the longitudinal axis 22 of the port 10 and defines a passageway that is oriented approximately parallel to the longitudinal axis 22 of the port, as indicated by arrow A in FIG. 3. The opening 30, in the exemplary embodiment, has length $l_s$ and a width $w_s$ that are selected to allow at least a portion of a fixation element, such as a spinal rod, to be manipulated from within the lumen 18 through the passageway defined by the opening 30. The opening 30 is positioned at the distal end 14 of the port 10 and has an open, i.e., unobstructed, distal end 32.

Figure 4:
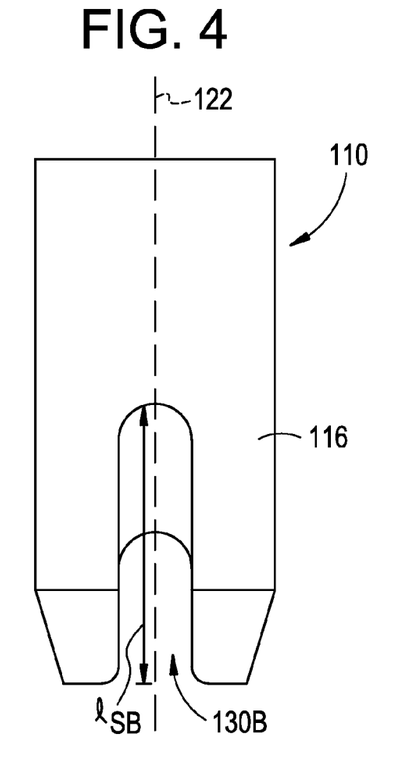
FIG. 4 is a front view of an exemplary embodiment of a surgical access port, illustrating a first opening formed in a sidewall of the port.
Figure 5:
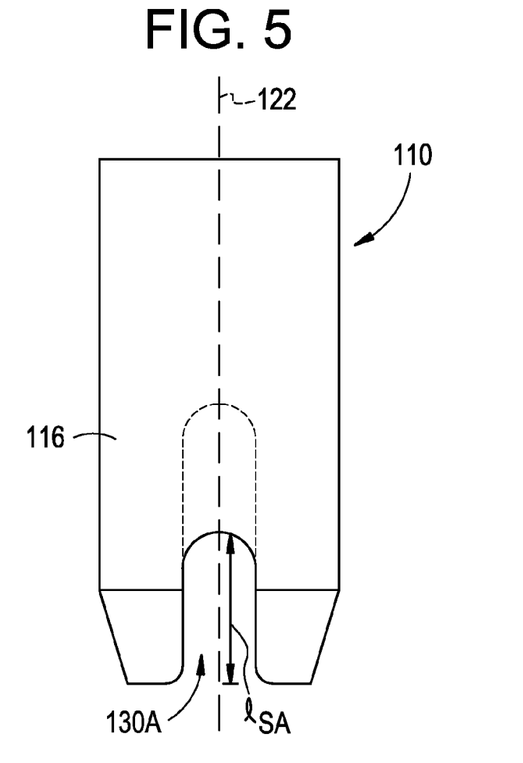
FIG. 5 is a rear view of the surgical access port of FIG. 4, illustrating a second opening formed in the sidewall of the port.
Figure 6:
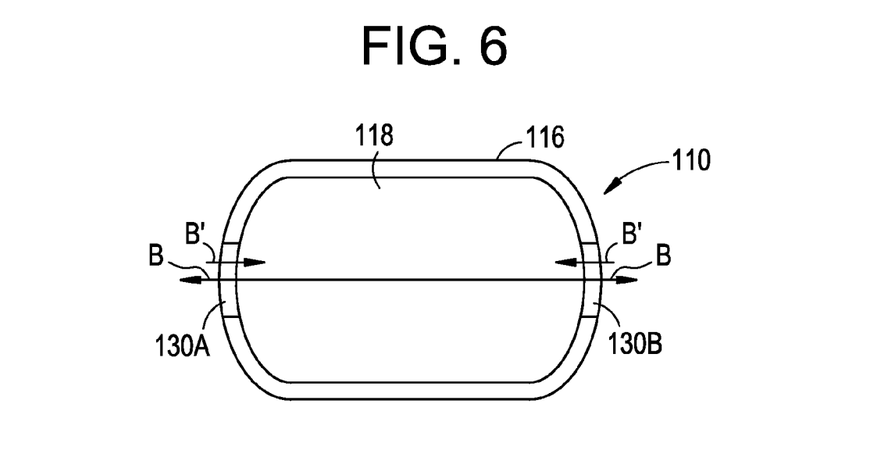
FIG. 6 is a bottom view of the surgical access port of FIG. 4.

FIGS. 4-6 illustrate an exemplary embodiment of a surgical access port 110 having two openings 130A, 130B formed in a sidewall 116 of the port 110 to facilitate passage of medical hardware between the lumen 118 of the port 110 and the exterior of the port 110. The size, shape, position, and number of the openings 130A,B may be varied depending on, for example, the procedure selected and the medical hardware employed. For example, the openings 130A,B may be sized, shaped, and positioned to facilitate delivery of a spinal fixation element, such as a plate, rod, cable, or tether, to a site exterior to the port 110 or to receive a spinal fixation element delivered to the lumen 118 of the port 110. The openings 130A,B in the exemplary port 110, are elongated slots extending proximally from the distal end 114 of the port 110. The openings 130A,B, in the illustrated embodiment, are oriented generally parallel to the longitudinal axis 122 of the port 110. The openings 130A, 130B are positioned generally opposite from each other, as illustrated in FIG. 6, and each opening 130A,B defines a passageway oriented approximately perpendicular to the longitudinal axis 122 of the port 110 for the passage of medical hardware, such as instruments or implants, out of the lumen 118 of the port 110, as indicated by arrows B, and/or into the lumen 118 of the port, as indicated by arrows B'. In the illustrated embodiment, for example, the length $l_{sa}$ of the first opening 130A is less than the length lsb of second opening 130B. In other exemplary embodiments, the length $l_{sa}$ of the first opening 130A may be equal to the length lsb of second opening 130B.

Figure 12:
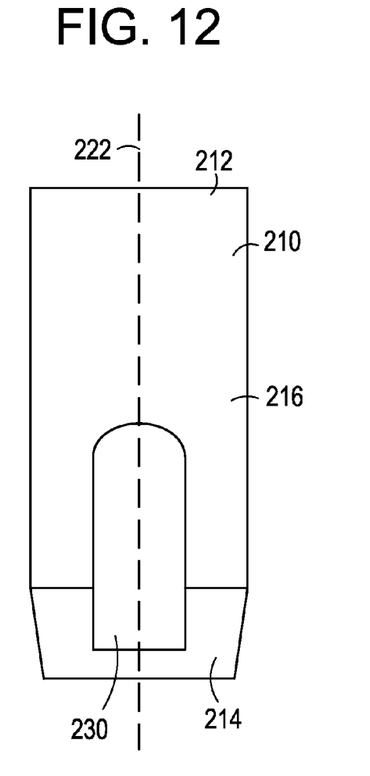
FIG. 12 is a front view of an exemplary embodiment of a surgical access port having an opening positioned between the distal end and the proximal end of the port.

FIG. 12 illustrates another exemplary embodiment of a surgical access port 210 having an opening 230 formed in a sidewall of the port 210. The opening 230 in the exemplary port 210 is an elongated slot that is oriented approximately parallel to the longitudinal axis 222 of the port 120 and is positioned between the distal end 214 and the proximal end 212 of the port 210. Unlike the exemplary ports 10, 110, described above, the opening 212 is not open at the distal end thereof. The position of the opening 230, as well as the size, shape, and number of opening(s) may be varied depending on, for example, the procedure selected and the medical hardware employed. For example, the opening 230 in the illustrated embodiment is positioned proximate the distal end 214 of the port 210. In other exemplary embodiments, the opening 230 may be positioned proximate the proximal end of the port 210.

Figure 13:
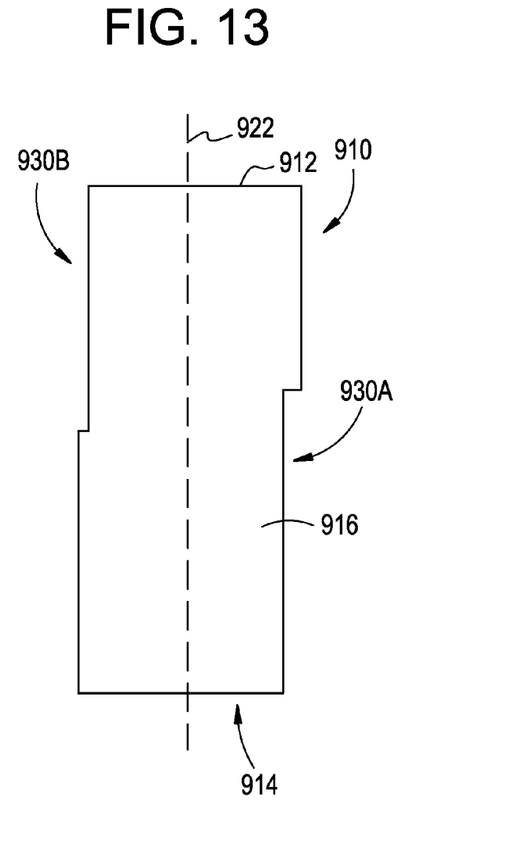
FIG. 13 is a side view of an exemplary embodiment of a surgical access port having a proximal opening and a distal opening.

FIG. 13 illustrates an exemplary embodiment of a surgical access port 910 having a plurality of openings 930A, 930B formed in the sidewall 916 of the port 910. In the illustrated exemplary embodiment, the port 910 includes a distal opening 930A extending proximally from the distal end 914 of the port 910 and a proximal opening 930B extending distally from the proximal end 912 of the port 910. In the illustrated exemplary embodiment, the distal opening 930A and the proximal opening 903B are opposed from one another and overlap along at least a portion of the longitudinal axis 922 of the port 910.

One skilled in the art will appreciate that the size, shape, position, orientation, and number of opening(s) is not limited to the embodiments described above. For example, the opening(s) may be circular, square, oval, or polygonal in shape and any number of openings may be employed.

In certain exemplary embodiments, the port may include indicia for indicating the location of the opening(s) on the port. For example, the proximal end 12 of the exemplary port 10 illustrated in FIGS. 1-3 may include one or more raised ridges 32 that indicate the position and orientation of the opening 30 in the sidewall 16 of the port 10. In the illustrated embodiment, a first ridge 32A is circumferentially aligned with the opening 30 and the second ridge 32B is diametrically opposed to the opening 30. In alternative embodiments, indicia for indicating the position of the opening in the sidewall of the slot may be a groove or mark on the proximal end and/or the sidewall or within the lumen of the port.

The surgical access ports disclosed herein may be employed to provide surgical access to the spinal anatomy. In one exemplary embodiment, a surgical access port, such as any of the exemplary ports described above, may be inserted, for example through an incision, into proximity to a first vertebra of the spine. For example, the distal end 14 of the surgical access port 10 illustrated in FIGS. 1-3 may be advanced into proximity to the first vertebra to define a first pathway to the first vertebra through the lumen 18 of the surgical access port 10. An instrument and/or implant may be advanced through the lumen 18 of the port 10 into proximity to the first vertebra to perform a procedure at the first vertebra or to perform a procedure at a location proximal to the first vertebra. Such procedures may be performed by manipulating an instrument and/or implant within the lumen 18 of the port 10 and/or by manipulating the instrument and/or implant through an opening 30 in the sidewall of the port 10. For example, an instrument and/or an implant may be advanced through the opening 30 to perform a procedure at the first vertebra or a position proximate the first vertebra, such as at a second vertebra that is adjacent to the first vertebra. Exemplary procedures include laminotomy, facetectomy, foraminotomy, nerve root retraction, discectomy, and/or positioning of a spinal implant such as a spinal fixation element, such as a plate, rod, or tether, an interbody fusion device, a nucleus replacement device, an artificial disc, and a fastener, such as a bone anchor.

In certain exemplary embodiments, the distal end of a surgical access port, such as any of the exemplary ports described above, may be moved between two or more locations to perform procedures at multiple sites. For example, the distal end 14 of the exemplary port 10 may be advanced, e.g., through an incision, into proximity to a first and second vertebrae. The proximal end 12 of the port 10 may be manipulated to move the distal end 14 into alignment with at least a portion of the first vertebra by, for example, angling the proximal end 12 relative to the skin incision in a procedure generally referred to as "wanding." A procedure may be performed at the first vertebra, such as, for example, placement of a first bone anchor in the first vertebra. The proximal end 12 of the port 10 may be manipulated to move the distal end 14 into alignment with at least a portion of the second vertebra and a procedure may be performed at the second procedure, such as, for example, placement of a second bone anchor in the second vertebra. A fixation element, such as a spinal rod, may be coupled to the first and second bone anchors using the surgical access port. For example, a first end of the fixation element may be positioned in the port and advanced through the lumen 16 to the opening 30. The first end of the fixation element may be advanced subcutaneously through the opening 30 toward the first vertebra. The fixation element may be coupled to the second anchor by, for example, delivering a closure mechanism, such as a set screw or cap, through the port 10 to the second anchor. The proximal end 12 of the port 10 may be manipulated to the move the distal end 14 into alignment with the first vertebra. During movement of the distal end 14 of the port 10 to the first vertebra, the opening may be aligned with the fixation element such that the distal end 14 moves along the fixation element toward the first vertebra. Once the distal end 14 of the port 10 is aligned with the first end of the fixation element may be positioned relative to the first anchor and the fixation element may be coupled to the first anchor.

The fixation element may be advanced within the lumen of the port and subcutaneously through the opening(s) in the port using any conventional instrument for manipulating a spinal fixation element. In certain exemplary embodiments, the fixation element may be advanced through the lumen of the port in orientation substantially parallel to the longitudinal axis of the port. The fixation element may be manipulated through the opening(s) in the port to an orientation that is angled with respect to the longitudinal axis of the port. In certain embodiments, the fixation element may be oriented substantially perpendicular to the longitudinal axis of the port. Exemplary instruments for manipulating a spinal fixation element between two or more orientations are disclosed in U.S. patent application Ser. No. 10/737,166, filed Dec. 16, 2004; U.S. patent application Ser. No. 10/737,538, filed Dec. 16, 2004; and U.S. Patent Application Ser. No. 60/542,548, filed Apr. 27, 2004, each of the aforementioned patent applications are incorporated herein by reference.

In certain exemplary embodiments, two or more surgical access ports, such as any of the exemplary ports described above, may be employed to provide access to multiple sites proximate the spine. For example, two surgical access ports may be employed to facilitate subcutaneous placement of a spinal fixation element between to or more vertebrae. In one exemplary embodiment, for example, a first port, such as exemplary port 10, may be inserted to define a first pathway to a first vertebra. A first bone anchor may be advanced through the lumen 16 of the first port 10 to the first vertebra. A second port, such as exemplary port 10, may be inserted to define a second pathway to a second vertebra, which, for example, may be adjacent the first vertebra. A second bone anchor may be advanced through the lumen of the second port to the second vertebra. A spinal fixation element, for example, a spinal rod, may be positioned in the lumen of the first port. An end of the spinal fixation element may advanced through an opening 30 of the first port 10 and advanced subcutaneously to an opening 30 in the second port. The spinal fixation element may be coupled to the first anchor by delivering a closure mechanism through the lumen 16 of the first port and to the second anchor by delivering a closure mechanism to the second anchor through the second port.

FIGS. 7-11 schematically illustrate an exemplary method of minimally invasive surgery that provides for the placement of multiple bone anchors and a fixation element on one or both sides of a patient's spine. The exemplary method may be employed to stabilize and align two or more bone segments, in particular, two vertebrae ($VB_1$, $VB_2$), in a minimally invasive manner that reduces trauma to adjacent tissue.

Figure 7:
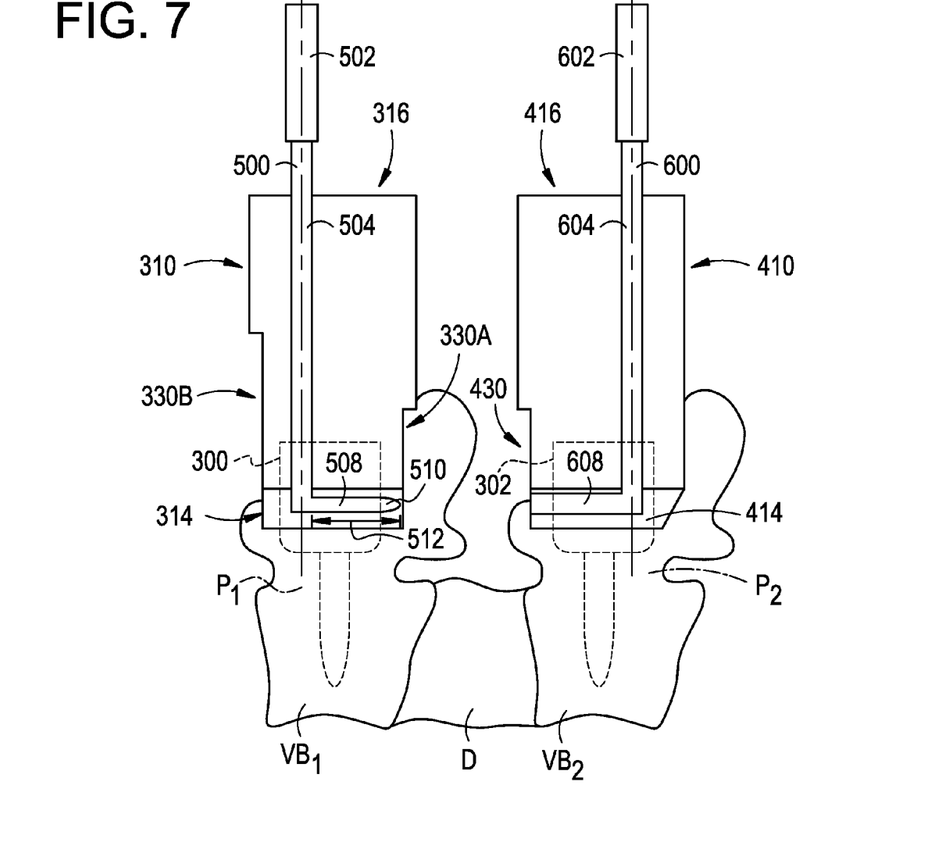
FIG. 7 is a side view in cross section of a first surgical access port and a second surgical access, illustrating an instrument system comprising a first instrument and a second instrument positioned in the ports to facilitate creation of a subcutaneous pathway between the ports.
Figure 8:
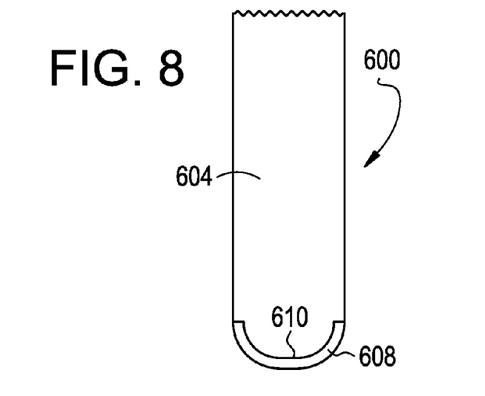
FIG. 8 is a front view of the second instrument of the instrument system illustrated in FIG. 7.

Referring to FIG. 7, the exemplary method may comprise making a first incision in a patient and positioning a first surgical access port 310, such as an exemplary surgical access port described above, in the first incision. In the illustrated embodiment, the first port 310 is analogous in construction to the exemplary surgical access port illustrated in FIGS. 4-6 and described above. The distal end 314 of the port 310 is advanced into proximity to a first vertebra $VB_1$ and the lumen 316 of the first port 310 defines a first pathway from the incision to the first vertebra $VB_1$.

The first incision may be a minimally invasive incision made in the patient's skin that is expanded, for example, by retraction and or dilation, to create a pathway from the first incision to the proximate the first vertebra $VB_1$. The first incision 14 may be expanded to create the pathway in any conventional manner. In certain embodiments, for example, the first incision may be expanded by dilation to the desired size, shape, and orientation. For example, the first incision may be sequentially dilated using a plurality of dilators to create the pathway to the first vertebra. Exemplary methods and instruments for serial dilation are described in commonly owned U.S. Pat. No. 6,159,179, entitled Cannula and Sizing and Insertion Method; U.S. patent application Ser. No. 10/024,221, filed Oct. 30, 2001, entitled Non-Cannulated Dilators; and U.S. patent application Ser. No. 10/021,809, filed Oct. 30, 2001, entitled Configured and Sized Cannulas, each of which is incorporated herein by reference. In other embodiments, a single dilator may be employed to expand the incision. Once dilation is concluded, the first port 310 may be positioned into the dilated first incision to define a first passageway to the vertebra. Alternatively, a retractor may be inserted into the dilated first incision to further expand the first incision and then the first port may be positioned in the first incision.

In certain exemplary embodiments, the first incision may be expanded by inserting one or more retractors into the incision and expanding the incision to the desired size, shape, and orientation by expanding the retractor accordingly. Any type of conventional retractor or retractors may be employed to expand the first incision. For example, suitable retractors are described in commonly owned U.S. patent application Ser. No. 10/815,182, filed Mar. 31, 2004, entitled Telescoping Blade Assemblies and Instruments for Adjusting an Adjustable Blade; U.S. Provisional Patent Application Ser. No. 60/530,655, filed Dec. 18, 2003, entitled Surgical Retractor Systems, Illuminated Cannula and Methods of Use; and U.S. patent application Ser. No. 10/808,687, entitled Surgical Retractor Positioning Device, each of which are incorporated herein by reference.

In certain exemplary embodiments, the first incision may be expanded to create a pathway by an intermuscular procedure that includes locating a muscle plane separating two muscles and separating the muscles at the muscle plane to create the first pathway. For example, in certain exemplary methods, the intermuscular plane separating the multifidus and longissimus muscles may be located through the first incision. The multifidus and longissimus muscles may be separated at the muscle plane by blunt dissection, for example, by inserting a finger or an instrument, such as a retractor, through the muscle plane and advancing the finger or instrument to the vertebra to create the pathway to the vertebra. Intermuscular procedures are described in detailed in U.S. Pat. No. 6,692,434, entitled Method and Device for Refractor for Microsurgical Intermuscular Lumbar Arthrodesis; U.S. patent application Ser. No. 10/060,905, filed Jan. 29, 2002, entitled Retractor and Method for Spinal Pedicle Screw Placement; and New Uses and Refinements of the Paraspinal Approach to the Lumbar Spine, L. L. Wiltse and C. W. Spencer, Spine, Vol. 13, No. 6, Nov. 6, 1988, each of which is incorporated herein by reference.

The first incision may be a percutaneous skin incision that has a shape and extent that is less than, equal to, or slightly greater than, the extent of the instruments and implants being inserted thereto. In certain exemplary embodiments, for example, the incision may be a stab incision that is expanded to facilitate positioning of the first port 310 therethrough.

Continuing to refer to FIG. 7, a first anchor 300 may be advanced through the first pathway defined by the lumen 316 of the first port 310 to an anchor site on the first vertebra $VB_1$. The first bone anchor 300 may be any type of conventional bone anchor, including, for example, a monoaxial or polyaxial bone screw, a bolt, or a hook. The first bone anchor 300 may be implanted into any portion of the first vertebra $VB_1$ respectively, in any conventional manner through the first incision. In the illustrated embodiment, the first bone anchor 300 is implanted into a first pedicle $P_1$ of the first vertebra $VB_1$.

A second surgical access port 410 may be inserted through a second incision to define a second pathway from the second incision to a second vertebra $VB_2$. In the illustrated embodiment, the second port 410 is analogous in construction to the first port except the second port 410 has a single opening 430 and the first port 310 has two openings 330A, 330B. The opening 430 in the second port may be aligned with at least one of the openings 330A, 330B in the first port 310 by, for example, rotating one or both of the ports. Alignment indicia on the proximal end of the ports may be employed to facilitate alignment of the openings. In the illustrated embodiment, the opening 430 in the second port 410 is aligned with the opening 330A of the first port 310.

The second incision may be expanded to create a pathway to the second vertebra $VB_2$ in a manner analogous to the first incision described above. The second incision may be a percutaneous skin incision in a manner analogous to the first incision.

Continuing to refer to FIG. 7, a second bone anchor 302, e.g., a polyaxial bone screw analogous to the first bone anchor, may be advanced through the second pathway defined by the lumen 416 of the second port 410 to a second anchor site on the second vertebra $VB_2$. The second bone anchor 302 may be implanted into any portion of the second vertebra $VB_2$ respectively, in any conventional manner through the second incision. In the illustrated embodiment, the second bone anchor 302 is implanted into a second pedicle $P_2$ of the second vertebra $VB_2$.

A spinal fixation element, for example, a spinal rod, may be positioned in the first port 310 and advanced subcutaneously through the opening 330A and the opening 430 to the second anchor 302. In the exemplary method, a first instrument 500 may be employed for creating a subcutaneous pathway between the first port 310 and the second port 410 to facilitate advancement of the spinal fixation element to the second anchor 302. The exemplary first instrument 500, as illustrated in FIG. 7, includes a proximal handle 502, a shaft 504 having a longitudinal axis 506, and a distal tip 508 that is oriented at an angle to the shaft 504 and is configured to dissect tissue. The shaft 504 of the exemplary instrument is preferably sized to fit through the lumen of the first port 310. The distal tip 508 may be oriented at an angle greater than or equal to approximately 45.degree. to the longitudinal axis 506 of the shaft 500, and, in the illustrated embodiment, is oriented approximately perpendicular to the longitudinal axis 506 of the shaft 500, although one skilled in the art will appreciate that other angles suitable for creating a subcutaneous pathway may be utilized. The distal tip 508, in the illustrated embodiment, terminates at a tip 510 suitable for dissecting tissue. The length of the distal tip 508, indicated by arrow 512 in FIG. 7, may be varied depending on the procedure and the anatomy. In the illustrated embodiment, for example, the length of the distal tip is selected to span the distance between the distal end 314 of the first port 310 and the distal end of the second port 410. In certain exemplary embodiments, the tip 510 of the instrument 500 may be sized to interface with a bone anchor positioned in the first port 310 and/or the second port 410. For example, the tip 510 of the instrument 500 may be sized to seat within the spinal fixation element receiving portion of the bone anchor. In the case of a polyaxial bone screw, for example, the tip 510 of the instrument 500 may be sized to seat within the spinal rod receiving slot of the polyaxial bone screw.

Continuing to refer to FIG. 7, the first instrument 500 may be manipulated to advance the distal tip 508 through the opening 330A in the first port 310 to create a subcutaneous pathway between the opening 330A in the first port 310 and the opening 430 in the second port 410.

In certain alternative embodiments, the spinal fixation element may have a tip configured to create a subcutaneous pathway. For example, the fixation element may be a spinal rod having a tip suitable for tissue dissection. Advancement of the spinal rod to the second anchor may create the subcutaneous pathway between the first port 310 and the second port 410.

In certain exemplary embodiments, including the illustrated embodiment, a second instrument 600 may be used in cooperation with the first instrument 500 to facilitate the creation of a subcutaneous pathway between the distal end 314 of the first port 310 and the distal end 414 of the second port 410. The exemplary second instrument 600, as illustrated in FIGS. 7-10, includes a proximal handle 602, a shaft 604 having a longitudinal axis 606, and a distal tip 608 oriented at an angle to the longitudinal axis 606 of the shaft 604. The shaft 604 of the exemplary second instrument 600 is preferably sized to fit through the lumen 416 of the second port 610. The distal tip 608 of the second instrument 600, in the illustrated embodiment, is oriented approximately perpendicular to the longitudinal axis 606 of the shaft 600, although one skilled in the art will appreciate that other angles suitable for creating a subcutaneous pathway may be utilized. The distal tip 608 may be sized to receive at least a portion of the distal tip 508 of the first instrument 500. For example, in the exemplary embodiment, the distal tip 608 of the second instrument 600 may be generally arcuate in cross-section and may include a proximal surface 610 for receiving the distal tip 508 of the first instrument 500. The proximal surface 610 may be complementary in size and shape to the distal tip 508 of the first instrument 500 to facilitate alignment of the distal tip 508 of the first instrument 500 and the distal tip 608 of the second instrument 600. For example, the proximal surface 610 may have a curvature analogous to the curvature of the distal tip 508 of the first instrument 500. In certain exemplary embodiments, the distal tip 508 of the first instrument 500 and the distal tip 608 of the second instrument 600 may be coaxially aligned when engaged with one another. One skilled in the art will appreciate the distal tip 608 of the second instrument 600 may have other configurations suitable for receiving the distal tip 508 of the first instrument 500. For example, the distal tip 608 of the second instrument 600 may be generally cylindrical in shape, having for example, a generally circular cross section, for receiving the distal tip 508 of the first instrument 500 in a telescoping relationship. In certain exemplary embodiments, the tip 610 of the instrument 600 may be sized to interface with a bone anchor positioned in the first port 310 and/or the second port 410. For example, the tip 610 of the instrument 600 may be sized to seat within the spinal fixation element receiving portion of the bone anchor. In the case of a polyaxial bone screw, for example, the tip 610 of the instrument 600 may be sized to seat within the spinal rod receiving slot of the polyaxial bone screw.

One skilled in the art will appreciate that use of the first instrument 500 and/or the second instrument 600 is optional. The first instrument 500 may be employed independent of the second instrument 600 to create a subcutaneous pathway between the distal end 314 of the first port 310 and the distal end 414 of the second port 410. As discussed above, in certain exemplary embodiments, the subcutaneous pathway may be created without instruments by, for example, advancement of the spinal fixation element from the first port to the second port.

Figure 9:
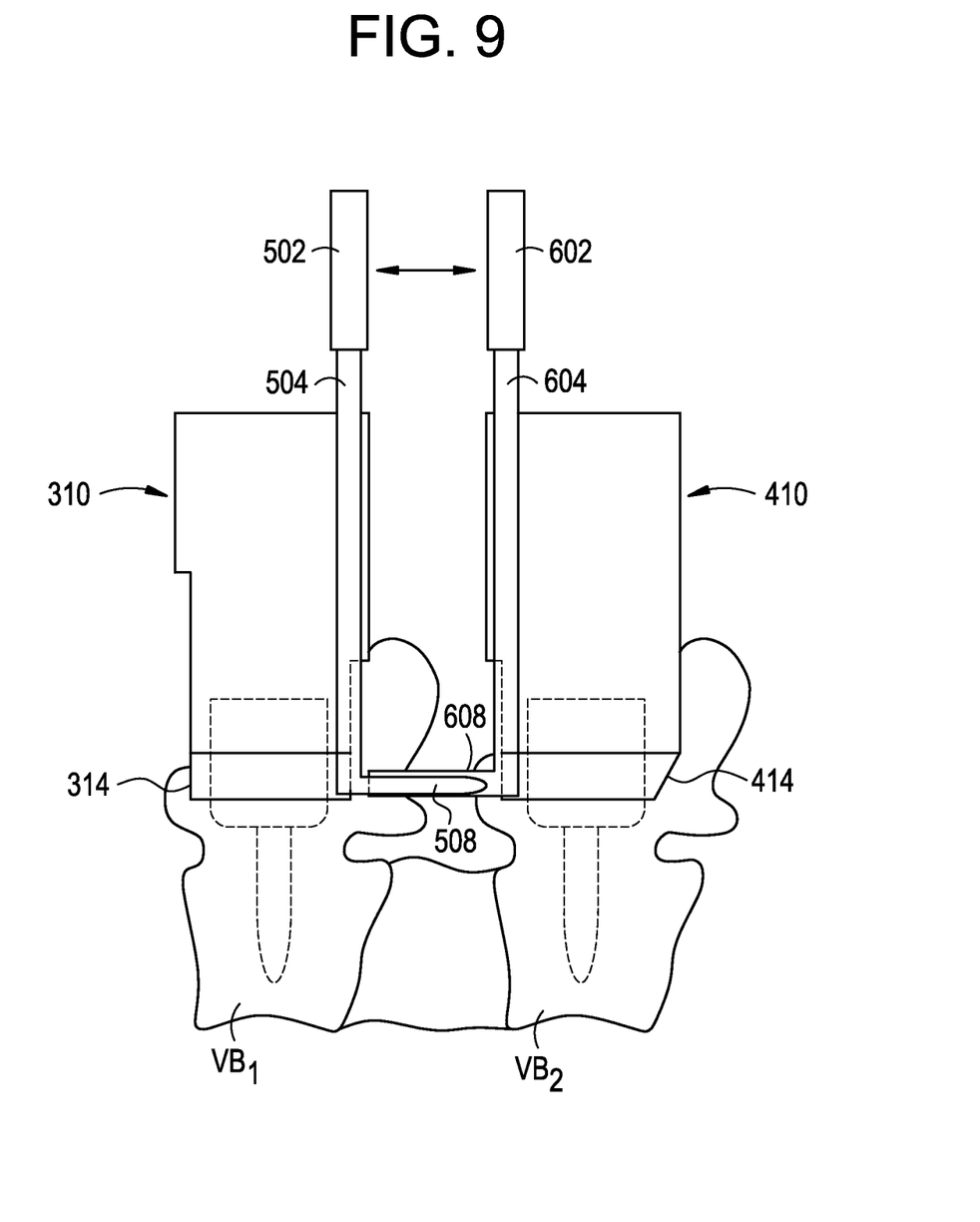
FIG. 9 is a side view in cross section of the ports of FIG. 7, illustrating the creation of a subcutaneous pathway between the ports.

In the exemplary method, the distal tip 508 of the first instrument 500 is advanced to the opening 430 in the second port 410 and into the distal tip 608 of the second instrument 600, thereby creating the subcutaneous pathway. As illustrated in FIG. 9, the first instrument 500 and the second instrument 600 may be cooperatively manipulated to facilitate creation and expansion of the subcutaneous pathway between the distal end 314 of the first port 310 and the distal end 414 of the second port 410. For example, the proximal handle 502 of the first instrument 500 and the proximal handle 602 of the second instrument 600 may be moved in unison to cause the distal tips 508, 608 to move in unison between the distal ends of the first and second ports 310, 410.

Figure 10:
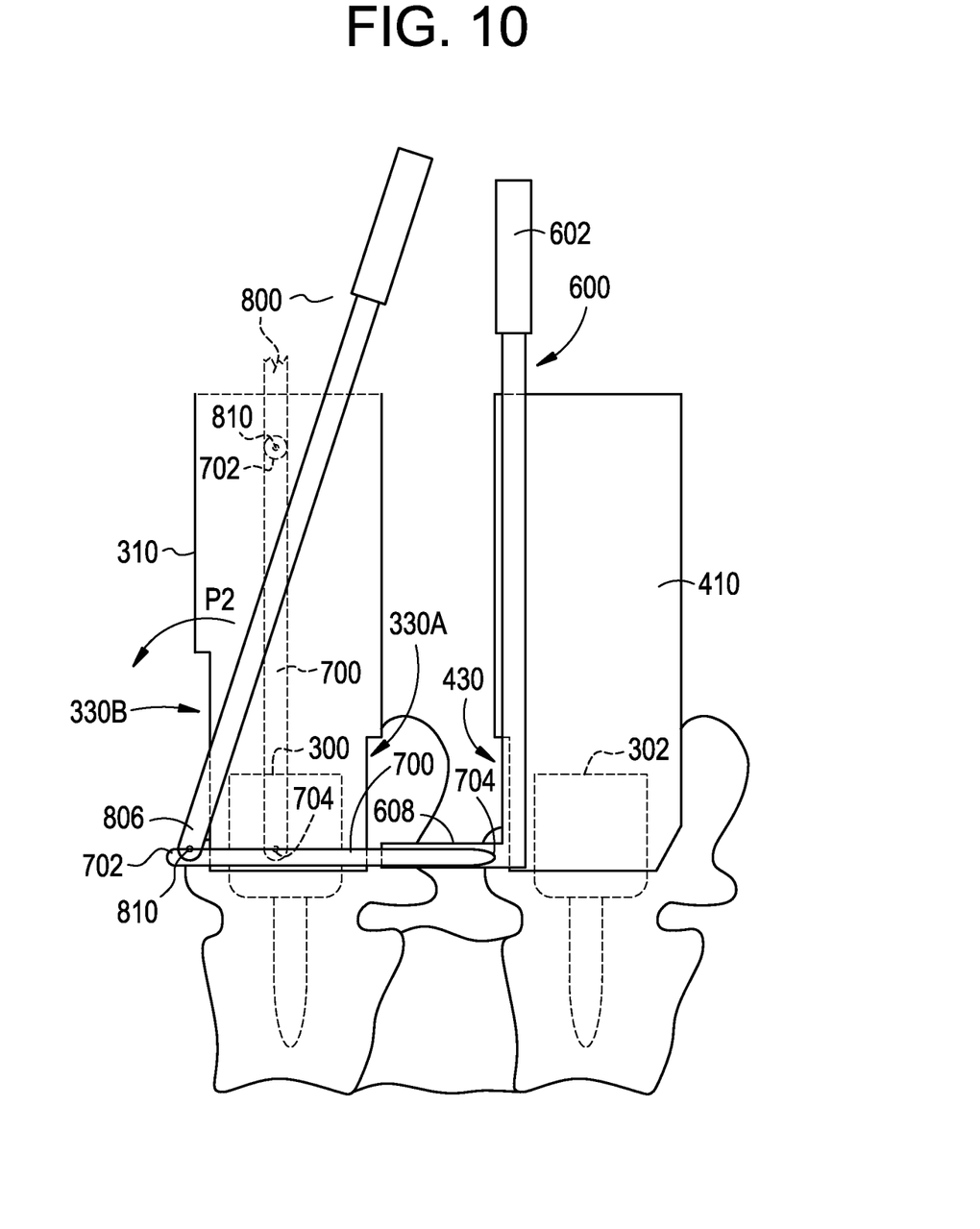
FIG. 10 is a side view in cross section of the ports of FIG. 7, illustrating the placement of a spinal rod along the subcutaneous pathway between the ports and between bone anchors positioned in the ports.

Referring to FIG. 10, a spinal fixation element, for example a spinal rod 700, may be advanced subcutaneously to the second anchor 302 using an instrument for manipulating a spinal fixation element, as described above. In the illustrated embodiment, an exemplary spinal rod manipulating instrument 800 includes a proximal handle 802, a shaft 804, and a distal end 806 that may be pivotally connected at a pivot point 810 to a first end 702 of the exemplary spinal rod 700. The exemplary rod manipulating instrument 800 allows the rod 700 to be positioned in the first port 310 in an orientation approximately parallel to the longitudinal axis of the first port 310 and to be pivoted to a non-parallel orientation to facilitate advancement of the rod 700 through a distal opening 330 in the port 310. In the exemplary embodiment, the rod 70 may be pivoted to an orientation that is substantially perpendicular to the longitudinal axis of the first port 310 to allow the second end 704 of the rod 700 to be advanced through the opening 330A and subcutaneously to the second port 410, as illustrated in FIG. 10. In the exemplary embodiment, the port 310 is provided with two opposed openings 330 A,B to facilitate transition of the rod 700 to an orientation suitable for subcutaneous advancement of the rod. For example, the opening 330A allows the first end 702 of the rod 700 to be pivoted to a non-parallel orientation, as illustrated by arrow P in FIG. 10. The manipulating instrument 800 may be employed to facilitate subcutaneous advancement of the rod 700 to the second port 410.

In certain exemplary embodiments, the second instrument 600 also may be employed to facilitate subcutaneous advancement of the rod 700 to the second port 410, as illustrated in FIG. 10. The distal tip 608 of the second instrument 600 may receive a portion of the rod 700, for example, the second end 704 of the rod 700, and may guide the rod 700 along the subcutaneous pathway to the second port 410. One skilled in the art will appreciate that use of the second instrument 600 is optional and that in certain exemplary embodiments the rod 700, or other fixation element, may be advanced to the second port 410 independent of an instrument positioned in the second port 410.

Figure 11:
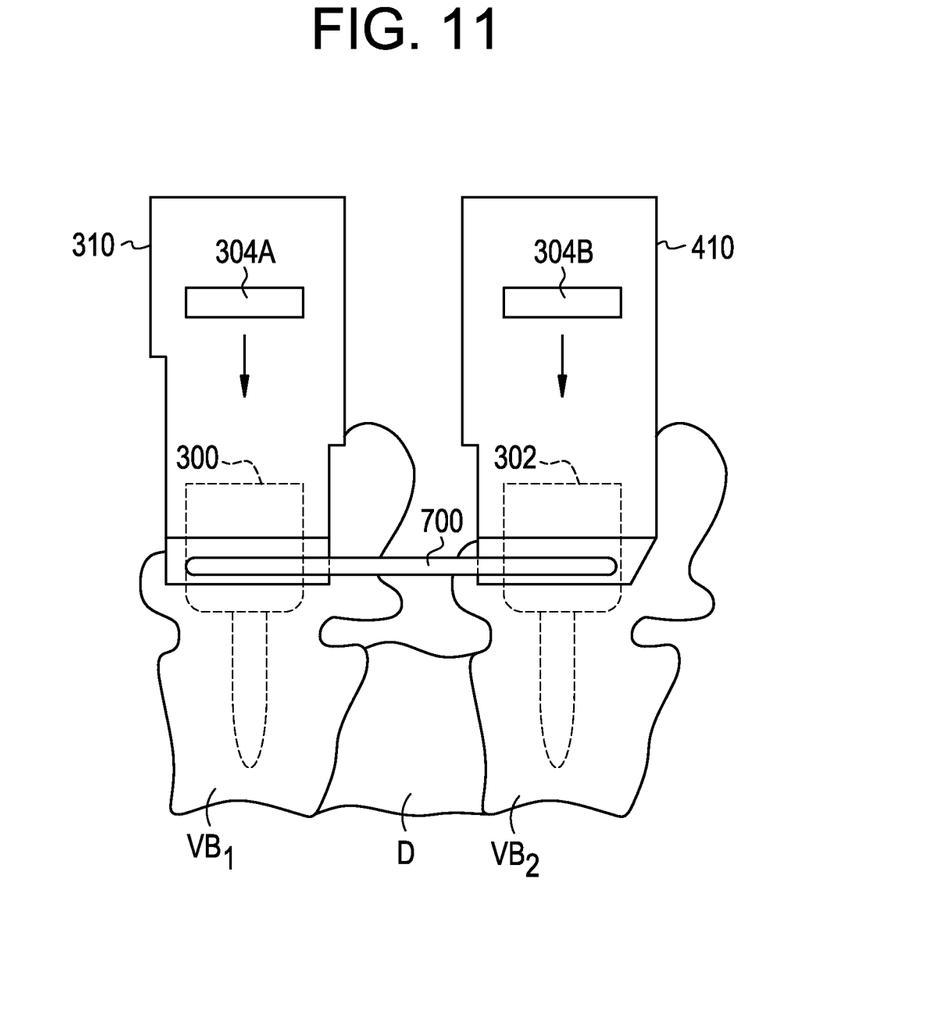
FIG. 11 is a side view in cross section of the ports of FIG. 7, illustrating the spinal rod in position between the ports.

Once the spinal fixation element, e.g., rod 700, is advanced to the second port 410, the fixation element may be coupled to the first anchor 300 and the second anchor 302. For example, a closure mechanism 304B may be advanced through the first port 310 to the first anchor 300 and a closure mechanism 304B may be advanced through the second port 410 to the second anchor 302, as illustrated in FIG. 11. The closure mechanisms may be coupled to the bone anchors to secure the spinal fixation element to the bone anchors.

In certain exemplary embodiments, the disk space D between the first and second vertebrae $VB_1$, $VB_2$ may be accessed though the first port 310 and/or the second port 410. For example, the distal end 314 of the first port 310 and/or the distal 414 end of the second port 410 may be moved into alignment with the disk space. In certain exemplary embodiments, the first port 310 and the second port 410 may be selected to have a size sufficient to provide access to a vertebra and the adjacent disk space. Accessing the disk space allows one or more procedures to be performed at the disk space. For example, all or a portion of the disk material may be removed from the disk space D. In certain embodiments, an interbody fusion device, including, for example, bone graft or a cage, may be placed in the disk space D to promote fusion of the first and second vertebrae $VB_1$, $VB_2$. In certain embodiments, an artificial disk may be placed in the disk space D.

In certain exemplary embodiments, the disk space D between the first and second vertebrae $VB_1$, $VB_2$ may be accessed through a separate incision, e.g., a third, incision, rather than the first incision through which the first port 310 is positioned and the second incision through which the second port 410 is positioned.

One skilled in the art will appreciate that the order of the steps of the exemplary method described in connection with FIGS. 7-11 is merely exemplary and the steps may be carried out in one or more different orders. For example, in certain exemplary embodiments, the subcutaneous pathway between the first port and the second port may be created before advancing the first anchor through the first port and before advancing the second anchor through the second port. In other exemplary embodiments, the subcutaneous pathway may be created after advancing the first anchor through the first port and before advancing the second anchor through the second port. In other exemplary embodiments, the first port and the second port may be placed before advancement of the first anchor and the second anchor through the ports.

While methods and instruments of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

What is claimed:

1. A system for minimally invasive spine surgery comprising:
    a plurality of bone anchors configured for implantation in a vertebra;
    a spinal rod configured to connect one bone anchor of the plurality of bone anchors implanted in a first vertebra with a second bone anchor of the plurality of bone anchors implanted in a second vertebra;
    a plurality of dilators of varying lengths and diameters;
    a first surgical access port comprising a proximal end, a distal end spaced apart a distance from the proximal end, and a sidewall defining a lumen extending from the proximal end to the distal end, the lumen having a length sufficient to at least span from a skin incision to proximate a vertebra and a diameter greater than the diameters of the plurality of dilators, the first surgical access port having a first opening formed in the sidewall, the first opening defining a passageway for medical hardware from the lumen to external to the first surgical access port;
    a second surgical access port comprising a proximal end, a distal end spaced apart a distance from the proximal end, and a sidewall defining a lumen extending from the proximal end to the distal end, the lumen having a length sufficient to at least span from a skin incision to proximate a vertebra and a diameter greater than the diameters of the plurality of dilators, the second surgical access port having a first opening formed in the sidewall, the first opening defining a passageway for medical hardware from the lumen to external to the second surgical access port;
    a first instrument for creating a subcutaneous pathway from the opening in the first surgical access port to the opening in the second surgical access port, the first instrument having a distal end sized to pass through the opening in first surgical access port and extend from the subcutaneously from a first vertebra to a second vertebra, and
    a second instrument having a distal end sized to pass through the opening in the second surgical access port and configured to engage the distal end of the first instrument.

2. The system of claim 1, wherein the second instrument further comprises a proximal handle, a shaft having a longitudinal axis, the shaft being sized to fit through the lumen of the second surgical access port and wherein the distal end of the second instrument is oriented at angle to the shaft and is sized to receive at least a portion of the distal end of the first instrument therein.

3. The system of claim 1, wherein the spinal rod has a tip configured to dissect tissue.

4. The system of claim 1, wherein the first instrument comprises a proximal handle, a shaft having a longitudinal axis, the shaft being sized to fit through the lumen of the port and wherein the distal end is oriented at angle to the shaft.

5. The system of claim 4, wherein the distal end is oriented approximately perpendicular to the longitudinal axis of the shaft.

6. The system of claim 4, wherein the distal end is sharpened sufficiently to dissect tissue.

7. A system for minimally invasive spine surgery comprising:
    a plurality of bone anchors configured for implantation in a vertebra;

a spinal rod configured to connect one bone anchor of the plurality of bone anchors implanted in a first vertebra with a second bone anchor of the plurality of bone anchors implanted in a second vertebra;

a plurality of dilators of varying lengths and diameters;

a first surgical access port comprising a proximal end, a distal end spaced apart a distance from the proximal end, and a sidewall defining a lumen extending from the proximal end to the distal end, the lumen having a length sufficient to at least span from a skin incision to proximate a vertebra and a diameter greater than the diameters of the plurality of dilators, the first surgical access port having a first opening formed in the sidewall, the first opening defining a passageway for medical hardware from the lumen to external to the first surgical access port;

a second surgical access port comprising a proximal end, a distal end spaced apart a distance from the proximal end, and a sidewall defining a lumen extending from the proximal end to the distal end, the lumen having a length sufficient to at least span from a skin incision to proximate a vertebra and a diameter greater than the diameters of the plurality of dilators, the second surgical access port having a first opening formed in the sidewall, the first opening defining a passageway for medical hardware from the lumen to external to the second surgical access port;

a first instrument for creating a subcutaneous pathway from the opening in the first surgical access port to the opening in the second surgical access port, the first instrument having a distal end sized to pass through the opening in first surgical access port and extend from the subcutaneously from a first vertebra to a second vertebra, the first instrument having a proximal handle, a shaft having a longitudinal axis, the shaft being sized to fit through the lumen of the port and wherein the distal end is oriented at angle to the shaft; and a second instrument having a distal end sized to pass through the opening in the second surgical access port and configured to engage the distal end of the first instrument, the second instrument having a proximal handle, a shaft having a longitudinal axis, the shaft being sized to fit through the lumen of the second surgical access port and wherein the distal end of the second instrument is oriented at angle to the shaft and is sized to receive at least a portion of the distal end of the first instrument therein.

8. The system of claim 7, wherein the distal end is oriented approximately perpendicular to the longitudinal axis of the shaft.

9. The system of claim 7, wherein the distal end is sharpened sufficiently to dissect tissue.

\* \* \* \* \*